United States Patent
Bunquin et al.

(10) Patent No.: US 9,120,741 B2
(45) Date of Patent: *Sep. 1, 2015

(54) TRANSITION METAL CATALYSTS FOR HYDROGENATION AND HYDROSILYLATION

(71) Applicant: GOVERNORS OF THE UNIVERSITY OF ALBERTA, Alberta (CA)

(72) Inventors: Jeffrey Camacho Bunquin, Alberta (CA); Jeffrey Mark Stryker, Alberta (CA)

(73) Assignee: Governors of the University of Alberta (CA)

( * ) Notice: Subject to any disclaimer, the term of this patent is extended or adjusted under 35 U.S.C. 154(b) by 75 days.

This patent is subject to a terminal disclaimer.

(21) Appl. No.: 13/725,735

(22) Filed: Dec. 21, 2012

(65) Prior Publication Data

US 2014/0179946 A1   Jun. 26, 2014

(51) Int. Cl.
| | | |
|---|---|---|
| *C07F 9/44* | (2006.01) | |
| *C07C 67/283* | (2006.01) | |
| *C07C 29/17* | (2006.01) | |
| *C07C 5/03* | (2006.01) | |
| *C07C 5/08* | (2006.01) | |
| *C07B 31/00* | (2006.01) | |
| *C07B 35/02* | (2006.01) | |
| *C07C 29/143* | (2006.01) | |
| *C07F 7/08* | (2006.01) | |
| *C07C 5/09* | (2006.01) | |

(52) U.S. Cl.
CPC ............ *C07C 67/283* (2013.01); *C07B 31/00* (2013.01); *C07B 35/02* (2013.01); *C07C 5/03* (2013.01); *C07C 5/08* (2013.01); *C07C 5/09* (2013.01); *C07C 29/143* (2013.01); *C07C 29/17* (2013.01); *C07C 29/172* (2013.01); *C07F 7/0829* (2013.01); *C07C 2101/18* (2013.01); *C07C 2531/18* (2013.01); *C07C 2531/28* (2013.01)

(58) Field of Classification Search
USPC ...................................... 556/479; 568/8, 480
See application file for complete search history.

(56) References Cited

U.S. PATENT DOCUMENTS

| | | | |
|---|---|---|---|
| 6,239,061 B1 | 5/2001 | Wang et al. | |
| 6,300,435 B1 * | 10/2001 | Gao et al. | 526/133 |
| 6,846,769 B2 | 1/2005 | Arndt-Rosenau et al. | |
| 2010/0168440 A1 * | 7/2010 | Shimizu et al. | 548/473 |
| 2012/0071700 A1 * | 3/2012 | Huang et al. | 585/259 |

FOREIGN PATENT DOCUMENTS

| | | |
|---|---|---|
| CA | 2605077 | 4/2009 |
| EP | 0881233 | 12/1998 |
| EP | 0890581 | 1/1999 |
| WO | WO 00/05236 | 2/2000 |
| WO | WO 00/05238 | 2/2000 |
| WO | WO 01/19512 | 3/2001 |
| WO | WO 2009/043156 | 4/2009 |
| WO | WO 2009/043157 | 4/2009 |

OTHER PUBLICATIONS

Dehnicke et al., "Phosphoraneiminato complexes of transition metals," Coordination Chemistry Reviews, 1999, vol. 182, Iss. 1, pp. 19-65.
Guérin et al., "Synthesis, Structure, and Reactivity of the Phosphinimide Complexes $(t\text{-}Bu_3PN)_nMX_{4-n}$ (M = Ti, Zr)," Organometallics, 2000, vol. 19, Iss. 16, pp. 2994-3000.
Klien et al., "Novel Imido- and Phosphorane-Imido-Nickel(II) Complexes. Crystal and Molecular Structure of $(\mu_3\text{-}NH)(\mu_3\text{-}NPMe_3)(NiClPMe_3)_3$," Journal of the American Chemical Society, 1991, vol. 113, pp. 4673-4675.
Mast et al., "Vinyl-type polymerization of norbornene by a nickel-based catalyst with phosphoraneiminato ligands," Macromolecular Rapid Communications, 1999, vol. 20, Iss. 4, pp. 232-235.
Ramos et al., "Titanium ferrocenyl-phosphinimide complexes," Dalton Transactions, 2010, vol. 39, Iss. 5, pp. 1328-1338.
Riese et al., Cobalt(II)-organische Phosphaniminato-Komplexe mit Heterocuban-Struktur. Kristallstrukturen von $[CoBr(NPR_3)]_4$ mit R = Me, Et, $[Co(C{\equiv}C\text{-}CMe_3)(NPMe_3)]4$ und $[Co(C{\equiv}C\text{-}SiMe_3)(NPEt_3)]_4$, Zeitschrift für anorganische und allgemeine Chemie (Journal of Inorganic and General Chemistry), 1998, vol. 624, Iss. 8, pp. 1279-1284.
Schroers et al., "Grafting of Vinyl-Type Polynorbornene on Polybutadiene and Polyisoprene," Macromolecular Chemistry and Physics, 2002, vol. 203, Iss. 18, pp. 2658-2664.
Yadav et al., "Phosphinimide complexes with pendant hemilabile donors: synthesis, structure and ethylene polymerization activity," Dalton Transactions, 2009, Iss. 9, pp. 1636-1643.

* cited by examiner

*Primary Examiner* — Sudhakar Katakam
*Assistant Examiner* — Pancham Bakshi
(74) *Attorney, Agent, or Firm* — Sheridan Ross P.C.

(57) ABSTRACT

Phosphoranimide-metal catalysts and their role in hydrogenation and hydrosilylation are disclosed. The catalysts comprise first row transition metals such as nickel, cobalt or iron. The catalysts have a metal to anionic phosphoranimide ratio of 1:1. This disclosure presents a process for catalytic hydrogenation and hydrosilylation of a range of unsaturated organic compounds under lower temperature and pressure conditions than conditions associated with industrial hydrogenation and hydrosilylation.

19 Claims, No Drawings

TRANSITION METAL CATALYSTS FOR HYDROGENATION AND HYDROSILYLATION

FIELD

This disclosure relates to soluble first row transition metal catalysts and the role of these catalysts in hydrogenation and hydrosilylation of a range of unsaturated organic functionality. More particularly, the catalysts have a phosphoranimide to metal ratio of 1:1, and are capable of catalyzing the hydrogenation and hydrosilylation of substrates having at least one unsaturated group.

BACKGROUND

Catalytic reduction of unsaturated organic substrates remains a key enabling industrial process that sustains major chemical industries. Fine chemicals production and petroleum upgrading, to name a few, are industries dependent on catalytic reduction of unsaturated organic compounds. Catalytic hydrogenation of unsaturated components of petroleum produces higher quality fuel components. In addition, the hydrogenation and hydrosilylation of a diverse set of unsaturated substrates produce value-added compounds for a wide range of applications. Industrial hydrogenation and hydrosilylation processes are commonly mediated by rare and expensive second- and third-row transition metal catalysts such as platinum, palladium, rhodium and ruthenium. The use of precious transition metals raises barriers to the economics and sustainability of these industrial processes. Hence, there remains a high demand for cost-effective catalyst technologies for hydrogenation and hydrosilylation.

Cheap and abundant first row transition metals are important candidates as economical and less toxic catalyst substitutes. First-row transition metal catalysts have traditionally been believed to possess intrinsically low activity. For example, most nickel-catalyzed hydrogenation reactions are generally much slower than precious metal-catalyzed reaction and require relatively harsh reaction conditions (e.g. 65 atm $H_2$ and 100° C.). However, results of studies on commercial $CoMoS_2$ catalysts can be interpreted to suggest that the active sites of the catalysts may be the cobalt rather than the molybdenum centers. Examples of these studies are detailed in papers such as (1) Duchet, J. C.; van Oers, E. M.; de Beer, V. H. J.; Prins, R. *J. Catal.* 1983, 80, 386; (2) Vissers, J. P. R.; de Beer, V. H. J.; Prins, R. *J. Chem. Soc. Farady Trans. I*. 1987, 83, 2145. These results suggest that catalysts containing transition metals such as cobalt may be useful in catalysis. In particular, late first-row transition metals such as Fe, Co and Ni are relatively inexpensive and abundant, making them good candidates for use in hydrogenation reactions.

SUMMARY OF THE INVENTION

According to one aspect, there is provided a method of catalyzing a hydrogenation or hydrosilyation reaction comprising: reacting an organic substrate having at least one unsaturated functional group in the presence of a reducing agent and a catalyst of general formula:

[M(NPR$_3$)]$_n$ where:

M is a first row transition metal having a +1 oxidation state; n is a whole number; $R_3PN^-$ is a monoanioinic phosphoranimide ligand of structure:

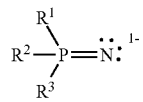

where:

$R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group containing at least one heteroatom; $R^1$, $R^2$, $R^3$ may also be linked to give cyclic systems; and wherein the M to $R_3PN^-$ ratio is 1:1.

According to one embodiment, the catalyst has the formula [M(NPR3)]n as defined above, and n is at least 2. In another embodiment, the catalysts has the formula [M(NPR3)]n as defined above and n is 2 to 8.

According to another aspect, there is provided a method of catalyzing a hydrogenation or hydrosilylation reaction comprising: producing a catalyst by reduction of a compound of Formula IV:

[M(NPR$_3$)X$_{(m-1)}$]$_n$    Formula IV where:

m=2 or 3; n=2 to 4; the M to $R_3PN^-$ ratio in Formula IV is 1:1; M is a first row transition metal selected from the group consisting of Co, Fe and Ni; $X^-$ can be any halide or pseudohalide; $R^1$, $R^2$, $R^3$ can be the same group or different groups; $R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom; and $R^1$, $R^2$, $R^3$ substituents may also be linked by aliphatic hydrocarbyl groups to give cyclic systems [(e.g., R1/R2=—(CH$_2$)$_n$—, where n=3-10]; and wherein the reducing agent used for the reduction of the complexes of Formula IV selected from the group of Li, Na, Na(Hg), Na-naphthalenide and K; and using the catalyst directly from the reduction reaction without subject to purification to catalyze the hydrogenation or hydrosilylation of a substrate having at least one unsaturated bond.

According to a third aspect, there is provided, a method of catalyzing the hydrogenation or hydrosilylation of an organic compound having at least one unsaturated group comprising: reacting the organic substrate with a compound selected from the group consisting of [Fe(NP$^t$Bu$_3$)]$_4$, [Co(NP$^t$Bu$_3$)]$_4$ and [Ni(NP$^t$Bu$_3$)]$_4$.

According to a fourth aspect, there is provided, a process for hydrogenation of an organic substrate having at least one unsaturated group: (i) combining the said organic substrate with a transition metal catalyst and a reductant, optionally in an inert solvent, to obtain a reaction medium; (ii) allowing for the catalytic hydrogenation or hydrosilylation of the substrate; (iii) obtaining the reduced products from the organic substrate; wherein the organic substrate is a compound containing at least one unsaturated group; wherein the ratio of catalyst to substrate is less than 1:1; and wherein the catalyst has the formula:

[M(NPR$_3$)]$_n$ where n is a whole number; the ratio of M to NPR$_3$ in the catalyst is 1:1; M is a first row transition metal selected from the group consisting of Fe, Co and Ni; NPR$_3$ is:

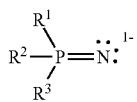

where:
R¹, R², R³ are independently alkyl (C1-18, primary, secondary or tertiary alkyl), cycloalkyl (C3-C8), aryl/heteroaryl, substituted aryl/heteroaryl or an inert functional group containing at least one heteroatom selected from the group consisting of a Group 14, Group 15 and Group 16; and wherein R¹, R², R³ may also be linked by aliphatic groups to give cyclic systems, [(e.g., R1/R2=—(CH$_2$)$_n$—, where n=3-10].

According to one embodiment, the catalyst has the formula [M(NPR3)]n as defined above, and n is at least 2. In another embodiment, the catalysts has the formula [M(NPR3)]n as defined above and n is 2 to 8.

DETAILED DESCRIPTION

The present disclosure relates to homogeneous ligand-supported coordinate complexes that function as catalysts for hydrogenation reactions. These catalysts of the present disclosure are coordinatively unsaturated. Coordinatively unsaturated catalysts are typically less stable and more reactive than coordinatively saturated catalysts, which make them suitable candidates for various organic transformations. The catalysts described herein comprise at least one metal having a formal oxidation state of +1 bonded to a monoanionic phosphoranimde ligand, the catalyst typically being in the form of a cluster of metal atoms, with the metal atoms bridged by the nitrogen atoms of the monoanionic phosphoranimide ligands. The metal atoms that comprise the catalysts are first-row transition metals.

The catalysts can function under relatively mild reaction conditions and can catalyze a range of reduction reactions. By "mild", it is meant temperature and pressure conditions that are lower than those typically associated with industrial catalysts. For example, the catalysts of the present disclosure operate at temperature ranges from about room temperature to about 200° C. and under pressure conditions from about 1 atmosphere to about 100 atmospheres of hydrogen gas, or below. As a person skilled in the art would appreciate, the reaction conditions for hydrogenation will necessarily vary, being dependent on the catalyst, the substrate and solvent used, among other factors. It has been observed that the present catalysts can function at higher pressure and temperature conditions than solely the mild conditions just described. Accordingly, in practice, the temperature and pressure range for functionality of the catalysts in quite broad.

The reduction process catalyzed by these catalyzed involves the formation of new C—H and/or C—Si and/or O—H and/or O—Si bonds, producing hydrogenation and/or hydrosilylation products from a range of unsaturated organic functionality.

The catalysts consist of an assembly of monomeric units having the empirical formula:

[M(NPR$_3$)]      Formula I where:
the ratio of M to NPR$_3$ is 1:1;
M is a first row transition metal;
NPR$_3$ is:

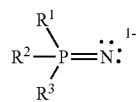

where:
R¹, R², R³ are independently alkyl (C1-18, primary, secondary or tertiary alkyl), cycloalkyl (C3-C8), aryl/heteroaryl, substituted aryl/heteroaryl or an inert functional group containing at least one heteroatom and wherein R¹, R², R³ may also be linked by aliphatic groups to give cyclic systems, [(e.g., R1/R2=—(CH$_2$)$_n$—, where n=3-10].

According to one embodiment, the transition metal may be Mn, Co, Ni or Fe. In the Examples, Ni, Fe and Co are shown to be suitable as metal centers.

According to one embodiment, the heteroatoms are Group 14, 15 and 16 elements, preferably Si, N or O.

The catalysts of the present disclosure will be referred to, throughout this disclosure, using the following general formula:

[M(NPR$_3$)]$_n$      Formula II where:
n is a whole number; and
M and NPR$_3$ are as defined above for the compound of Formula I.

In one embodiment, n is a whole number of at least 2. In another embodiment, n=2 to 8.

The [M(NPR$_3$)]$_n$ complex can adapt various modes of aggregation to form clusters. The present disclosure further discloses catalysts having the general formula:

[M(NPR$_3$)]$_4$      Formula III wherein M, NPR$_3$ are as defined above for the compound of Formula I.

As a specific, non-limiting example, the catalysts of Formula III are discrete tetrametallic transition metal clusters having the following structural formula:

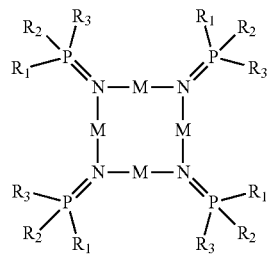

The metal centers of the catalysts of Formula III are supported by bridging, anionic phosphoranimide ligands. Each tetrametallic cluster consists of four nitrogen-bridged phosphoranimidometal(I) (i.e., MNPR$_3$) monomers.

As a person skilled in the art would appreciate, complexes of Formula II can adapt various modes of aggregation. As a result, the compound of Formula II represents a library of catalysts. Structurally characterized compounds of Formula III comprise a subclass of catalysts of Formula II. Compounds of Formula III result from the aggregation of four monomeric units of Formula I. Catalysts supported with phosphoranimide ligands of similar electronic and steric properties with, for example, tri-t-butylphosphoranimide, may adopt a tetrameric structure. However, unless specifically provided in the Examples, the catalysts of the present disclosure do not represent one particular characterized structure.

Based on the structure of Formula III catalysts, it should be apparent that the phosphoranimide (P=N) functional group displaces R1, R2 and R3 at a considerable distance away from the metal center, allowing for steric accessibility of substrates to the metal center(s). Thus, the metal center is still active, despite the presence of bulky substituents on the phosphoranimide. Each metal center in the Formula III catalysts has a coordination number of 2 and an oxidation state of +1. The steric accessibility and low-valent nature of the metal centers result in enhanced activity toward reductive transformations such as hydrogenation.

As a specific example, in the compounds of Formula I, II, III (discussed above) and IV (discussed below), trialkyl- and triarylphosphoranimides can impart thermal stability depending on the phosphorous substituents. Other substituents can be expected to impart similar stability as well, thus providing for the range of catalysts that can be used for the hydrogenation and hydrosilylation processes described herein.

Definitions

In the compounds of Formula I, II and III above and Formula IV (discussed below), as used herein, the term "alkyl" includes $C_1$ to $C_{18}$ straight chain, branched or cyclic alkyl groups such as, but not limited to, ethyl, propyl, isopropyl and t-butyl.

In the compounds of Formula I, II and III above, and Formula IV (discussed below), as used herein, the term "aryl" includes aromatic hydrocarbons as substituents. Aryl groups may have one or more aromatic rings which may be fused or connected by a connecting group or a bond. Specific examples include, though non-limiting, phenyl, tolyl, naphthenyl and biphenyl.

In the compounds of Formula I, II and III above and Formula IV (discussed below), as used herein, the term "heteroaryl" includes aromatic hydrocarbons which contain at least one heteroatom. Similar to the aryl groups, heteroaryls may have one or more aromatic rings which may be fused or connected by a connecting group or a bond.

In the compounds of Formula I, II and III above and Formula IV (discussed below), the term "inert functional group" is used to designate heteroatom-bearing hydrocarbyl fragments attached via the heteroatom to aromatic or heteroaromatic ligand substituents, as defined above, or appended to the terminus of a ligand substituent. The former serve to modulate, electronically and/or sterically, the chemical nature of the phosphoranimide ligand(s), modifying but not impeding catalyst performance. The latter can function as a point of further chemical attachment(s) (i.e., derivatization), for example, in order to construct supported heterogeneous catalysts comprising chemically bonded or linked phosphoranimido metal catalyst subunits grafted onto conventional catalyst supports.

As used herein, the term "derivative" is a functionalized version of a substrate where the substituent R's are not all hydrogen.

In the compounds of Formula I, II and III above and Formula IV (discussed below), as used herein, the term "heteroatom" is a Group 14 (except C), 15 or 16 element, preferably N, O, and Si.

In the compounds of Formula I, II and III above and Formula IV (discussed below), as used herein, the term "unsaturated group" or "unsaturation" is a multiple bond comprising double bonds and/or triple bonds. In the embodiments of the present invention, the unsaturated functional groups are carbon-carbon double bonds, carbon-oxygen double bonds and carbon-carbon triple bonds.

Hydrogenation and Hydrosilylation Catalysts

An embodiment of the present disclosure describes a process for hydrogenation of a compound having at least one unsaturated group. The process involves contacting the substrate having at least one unsaturated group with a metal catalyst of Formula II (i.e. $[MNPR_3]_n$), as defined above, in the presence of a reducing agent to effect the delivery of hydrogen atoms to the unsaturated group. This leads to the formation of new E-H bonds (where E=C, O or N), producing the products of hydrogenation. The process can be carried out optionally in the presence of an inert solvent. When using high-melting substrates, it is suitable to use an inert solvent.

Thus, the catalysts are useful for industrial hydrogenation reactions. The catalysts hydrogenate unsaturated organic substrates representative of some components of petroleum. The catalysts hydrogenate aliphatic (non-aromatic) carbon-carbon double bonds and carbon-carbon triple bonds, forming saturated hydrocarbons as terminal products. This, inter alia, is a key process for the industrial production of higher-quality liquid fuels during petroleum upgrading, as saturated compounds generally have higher octane ratings (i.e., combustion efficiency). Internal alkynes are hydrogenated into alkenes or alkanes or a mixture of the two, consisting of partially and completely hydrogenated organic products. For example, 1,2-diphenylacetylene can be hydrogenated to produce 1,2-diphenylethene, predominantly in the cis configuration, or 1,2-diphenylethane or a mixture of 1,2-diphenylethene and 1,2-diphenylethane. The extent of substrate conversion and the product distribution vary with the type of substrate, choice of catalyst, reaction time, concentration, among other factors. The appropriate reaction conditions for hydrogenation of a specific substrate should be apparent to a person skilled in the art based on the teachings of this disclosure and knowledge of basic principles in transition metal catalysis.

In addition, mono-, di- and trisubstituted alkenes can be similarly hydrogenated into the corresponding alkanes. For example, allylbenzene can be hydrogenated quantitatively into propylbenzene. Moreover, the catalysts hydrogenate esters containing unsaturated alkyl groups. This process, which produces saturated esters, is important for the production of foods and pharmaceutical products.

In another embodiment, the catalysts effect industrial hydrosilylation of organic substrates containing at least one unsaturated group. The process involves contacting the substrate with at least one unsaturated group with a metal catalyst of Formula II (i.e. $[MNPR_3]_n$), as defined above, in the presence of an organic silane (silyl hydride) to cause the reducing agent to react with the metal catalyst, resulting in the delivery of hydride(s) and/or silyl groups to the unsaturated functionality of the organic substrate. This leads to the formation of new bonds such as E-H and/or E-Si bonds (where E can be C, O or N), producing hydrogenation and hydrosilylation products. The process can be carried out optionally in the presence of an inert solvent.

The catalyst selectivity for hydrosilylation over hydrogenation varies with substrate type. For example, polar unsaturated bonds are preferentially converted to the hydrosilylation products under mild conditions. For example, the reduction of alkyl ketones in the presence of phenylsilane results in the formation of a mixture of products where alkoxysilanes are the major components while alcohols, the products of C=O hydrogenation, are minor component(s). This process is useful for the production of industrially important organosilicon compounds such as alkoxysilanes. In the case of nonpolar unsaturated bonds, such as alkenes and alkynes, the catalysts show low to moderate selectivity for the formation of the hydrosilylation product. For example, internal alkynes are hydrosilylated to give a mixture of alkenes and/or alkanes (hydrogenation products) and/or alkene-substituted vinylic silanes (hydrosilylation products). Moreover, substrates that contain both polar and nonpolar unsaturated groups, such as enones, are preferentially converted to the C=O hydrosilylation products, giving only minor formation of the C=C hydrogenation products. This process is of particular utility in fine chemicals synthesis where selective reduction of polar unsaturated groups in the presence of nonpolar groups may be desired.

The catalytic reduction reactions described herein may be carried out, optionally, in an inert organic solvent. By "inert", it is meant that the solvent does not react with or deactivate the catalyst or interfere materially in the hydrogenation process. Solvents such as toluene, xylene, decaline, methylnaphthalene or tetrahydrofuran (THF) have been used for certain examples. Toluene and THF have been generally used in the examples described herein. Halogenated solvents such as, but not limited to, dichloromethane ($CH_2Cl_2$) should generally be avoided. In some embodiments, where the unsaturated organic substrate is a liquid or low-melting solid, for example, an organic solvent may not be needed in the reaction. Reactions may also be run under triphasic conditions, also called the slurry phase, where some of the substrate, some of the catalyst, or some of each component is not completely dissolved in the selected solvent. The choice of solvent will vary with the properties of the substrate(s) under reduction.

The chemical reducing agent can be hydrogen ($H_2$) or an organic silane (silyl hydride). In the case of hydrogen, the reactions are routinely carried out in the presence of an excess of the reductant ($H_2$), employing pressures of less than 1 atm or higher. When an organic silane is used as the reducing agent, the silane may be chosen from the group consisting of phenylsilane, dimethylphenylsilane and ethylsilane, for example. The hydrosilylation reactions are preferentially carried out by adding a minimum of one equivalent of the silane for every molar equivalent of unsaturated group(s) in the substrate. In the case of substrates with one unsaturated group, for example trans-stilbene, the ratio of the substrate to the reductant may range from about 1:1 to 1:2 to ensure complete reaction.

In addition, the reaction can be carried out from somewhat below ambient temperature to around 200° C. For example, temperatures of about 20 to 150° C. may be used in some circumstances. The optimal temperature for the reaction will vary depending on the reactor design, reaction scale, solvent(s), reaction time and chemical feedstock. Optimum reaction temperature can be determined by those skilled in the art, using the teachings of this disclosure. As noted above, the temperature and pressure conditions described herein are milder than those typically employed in many industrial hydrogenation reactions.

All catalyst loadings where the catalyst to substrate ratio is less than about 1:1 can be used for catalytic hydrogenation. The catalysts are stable under a range of conditions and accordingly, a range of catalyst to substrate ratios may be used. For example, the catalyst loadings detailed in the Examples range from less than about 1:130 to about 1:15. Suitable catalyst-to-substrate ratios may vary with the specific catalyst, concentration, reaction time, and feedstock, among other factors, and can be determined by a person skilled in the art.

Purified Catalysts

The reduction of a range of organic substrates with at least one unsaturated group may be conducted using a purified catalyst of Formula II (i.e. $[MNPR_3]_n$). A "purified catalyst" is that subjected to at least some post-synthesis purification procedure(s). The Examples exemplify some purification procedures that may be suitable in this regard. The purity of the catalysts may be determined via elemental analysis prior to use for catalytic hydrogenation and hydrosilylation.

When using the purified catalysts, an organic molecule with at least one unsaturated group is contacted with a purified catalyst in the presence of a reducing agent. This causes the reducing agent to react with the metal catalyst, resulting in the delivery of hydride and/or silyl groups to the unsaturated functionality. Hydrogenation and hydrosilylation products are produced.

In-Situ Prepared Catalysts

An in situ-prepared (or in situ-derived) catalyst may be used in hydrogenation and hydrosilylation reactions. By "in situ", it is meant that the catalyst is not subject to purification after synthesis. In this embodiment, the catalyst of Formula II $[M(NPR_3)]_n$ is synthesized in situ and used for hydrogenation or hydrosilylation directly, without isolation or purification. The in situ-derived catalyst is produced through the chemical reduction of metal-phosphoranimide complexes (General Reaction II) having the general formula:

$$[M(NPR_3)X_{(m-1)}]_n \quad \text{Formula IV}$$

where:
m=2 or 3;
n=2 to 4;
the M to $R_3PN^-$ ratio is 1:1;
M is a first row transition metal;
$X^-$ can be any halide or pseudohalide;
$R^1$, $R^2$, $R^3$ can be the same group or different groups;
$R^1$, $R^2$, $R^3$=alkyl (C1-18, primary, secondary and tertiary alkyl), cycloalkyl (C3-C8), aryl/heteroaryl, substituted aryl/heteroaryl or an inert functional group optionally containing at least one heteroatom; and
$R^1$, $R^2$, $R^3$ substituents may also be linked by aliphatic hydrocarbyl groups to give cyclic systems [(e.g., R1/R2=—$(CH_2)_n$—, where n=3-10].

In one embodiment, the first row transition metal may be Mn, Co, Ni or Fe. In the Examples, Ni, Co and Fe are suitable transition metals.

In one embodiment, the halide or psuedohalide is $F^-$, $Cl^-$, $Br^-$, $I^-$, $OSO_2R^-$ (R=Me, Ph, p-Tol, $CF_3$).

The in-situ preparation of the catalyst of Formula II is carried out by treating a complex of Formula IV as defined above with an appropriate amount of a chemical reducing agent. The synthesis of this in situ-derived catalyst is conducted as shown below:

where:
$[M(NPR_3)X_{(m-1)}]_n$ is a halide-functionalized metal-phosphoranimide complex of Formula IV as defined above;
[H] is a chemical reducing agent; and
$[M(NPR_3)]_n$ is the metal-phosphoranimide catalyst of Formula II as defined above.

"Chemical reducing agents" are define here as different categories of reagents used in the two classes of reduction reactions described herein: (1) The chemical reducing agents required to effect the hydrogenation and/or hydrosilylation of unsaturated substrates include hydrogen ($H_2$) or an organic silane (silyl hydride); (2) the chemical reducing agents used to prepare the in situ-derived catalyst of Formula II

[M(NPR$_3$)]$_n$ may be a metal such as, but not limited to, Li, Na, or K. It should also be apparent to a person skilled in the art that metal reducing agents may exist in various compounded forms such as, but not limited to, sodium naphthalenide, Na(Hg) amalgam, Na—K alloy, or KC$_8$.

The preparation of the catalyst of Formula II can be carried out in inert organic solvents such as tetrahydrofuran, hexane, benzene, diethyl ether or toluene, for example. However, halogen-containing solvents, such as CH$_2$Cl$_2$, for example, are generally unsuccessful in this reduction step.

The ratio of the reducing agent to the total amount of metal in the complex of Formula IV [M(NPR$_3$)X$_{(m-1)}$]$_n$ may vary depending on the initial oxidation state of the precursor and the specific reducing agent. For example, when the reducing agent is Na(Hg) amalgam, the ratio of the reducing agent to complexes of Formula III can range from, but is not limited to, about 1:1 to 2:1. Ratios higher than of this can be also used for the reduction, but are not necessary. The reduction may be carried out in solvents selected from the group of, but not limited to, tetrahydrofuran, dialkyl ethers, toluene or saturated hydrocarbons such as pentane and hexane.

The reduction step can be conducted at low to ambient temperatures. By "low", it is meant temperatures below about 0° C. and by "ambient", it is meant about room temperature. The preferred temperature for the reduction step will vary with the complex of Formula IV, the solvent used, the concentrations of the various components, and the choice of reducing agent. A person skilled in the art would be able to determine the appropriate reaction temperature. For example, temperatures may range from about −80 to 25° C., when the reaction is carried out in an inert organic solvent. As a specific but non-limiting example, the reduction of [Cl$_2$Co$_2$(μ-NP$^t$Bu$_3$)$_2$(THF)$_2$] using 1% Na(Hg) amalgam and leading to [Co(NP$^t$Bu$_3$)]$_4$ as the product, may be carried out at about −35° C.

The solution from the reduction process, containing the in situ-derived catalyst, [MNPR$_3$]$_n$, is directly used for hydrogenation or hydrosilylation without carrying out the purification procedures described for the synthesis of purified and well-characterized catalysts of Formula II (i.e. [MNPR$_3$]$_n$.) and in the synthesis of a compound of Formula I (i.e. MNPR$_3$]$_n$).

The in situ-prepared catalyst hydrogenates organic substrates with at least one unsaturated group under similar reaction conditions as described above using purified catalyst. The process pertains to contacting an organic molecule with at least one unsaturated group with in situ-prepared catalyst in the presence of a reducing agent to cause the reducing agent to react with the metal catalyst, delivering hydrogen atoms and/or a silyl group to the organic substrate having at least one unsaturated group, to form hydrogenation and/or hydrosilylation products. The process can be carried optionally in the presence of an inert organic solvent for the same reasons described above pertaining to the use of "pure catalysts" for hydrogenation. The reaction conditions for use of the in situ-prepared catalyst are similar to those conditions described above for the purified catalysts.

In another aspect, there is disclosed a method for the synthesis of the in-situ-derived catalyst of Formula II [M(NPR$_3$)]$_n$ from an anionic metathesis reaction between a metal halide (MX$_m$) and an alkali or alkaline metal salt of a phosphoranimide ligand, followed directly by the reduction of this intermediate, as described above The metal precursor can be a metal salt such as MX$_m$ or a solvated metal salt such as L$_a$MX$_m$. This reaction is as illustrated below:

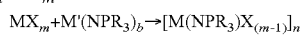

MX$_m$+M'(NPR$_3$)$_b$→[M(NPR$_3$)X$_{(m-1)}$]$_n$

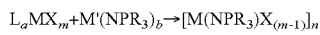

L$_a$MX$_m$+M'(NPR$_3$)$_b$→[M(NPR$_3$)X$_{(m-1)}$]$_n$ where:

M'(NPR$_3$)$_b$ is a Group I or Group II metal phosphoranimide salt and wherein the anionic phosphoranimide R$_3$PN—ligand is as defined above; and m=2 to 3;
n=1 to 4;
a=1 to 3;
b=1 or 3

M to R$_3$PN ratio in the complex of formula [M(NPR$_3$)X$_{(m-1)}$]$_n$ is 1:1;

M can be any first row transition metals;

X$^-$ can be any halide or pseudohalide;

L can be a two-electron dative donor molecule selected from the group of dialkyl ethers such as, but not limited to, tetrahydrofuran, 1,2-dimethoxyethane, dioxane; or selected from the group of trialkylphosphine or a triarylphosphine such as, but not limited to triphenylphosphine or tri-(p-tolyl)phosphine; and M' can be an alkali or alkaline metal. Alkali phosphoranimide salts (i.e. M'(NPR$_3$)$_b$) employed in the synthesis can include monophosphoranimide salts of lithium, sodium, potassium, and cesium; and alkaline earth metal phosphoranimide salts can include [Mg(NPR$_3$)$_2$] and [Mg(NPR$_3$)X].

In one embodiment, the first row transition metal may be Co, Ni, Fe or Mn. In the example, Ni, Co and Fe are found to be suitable metals.

In one embodiment, the halide or pseudohalide may be F$^-$, Cl$^-$, Br$^-$, I$^-$, OSO$_2$R$^-$ (R=Me, Ph, p-Tol, CF$_3$), for example.

In general, the synthesis of complexes of general formula [M(NPR$_3$)X$_{(m-1)}$]$_n$ requires a M to R3PN$^-$ ratio of about 1:1 or greater. The suitable ratio of the metal salt to M'(NPR$_3$)$_b$ varies with the specific metal, leaving group (X) and M'(NPR$_3$)$_b$ reagent. When b=1 or when a [Mg(NPR$_3$)X] reagent is used, the ratio of the metal salt to M'(NPR$_3$)$_b$ can be about a 1:1 ratio; however, yields are generally higher in the presence of an excess of the metal salt, for example, at a ratio of 2:1. When b=2, the excess of metal salt is maintained in the range from about 2:1 to about 4:1 to ensure that the M to R3PN$^-$ ratio in the product is about 1:1.

The anionic metathesis can be conducted in low to ambient temperatures. For example, temperatures may range from about −80 to about 25° C. when the reaction is carried out in an inert organic solvent. The anionic metathesis reaction is preferably conducted at temperature ranging from about −75 to about −35° C., as demonstrated in the synthesis of [Co(NP$^t$Bu$_3$)]$_4$ and [Ni(NP$^t$Bu$_3$)]$_4$ described herein.

Definitions Used in Reaction Substrates

In the unsaturated substrates described herein, the term "alkyl" includes C$_1$ to C$_{18}$ straight chain, branched or cyclic alkyl groups such as, but not limited to, ethyl, propyl, isopropyl and t-butyl.

In the unsaturated substrates described herein, the term "aryl" includes aromatic hydrocarbons as substituents. Aryl groups may have one or more aromatic rings which may be fused or connected by a connecting group or a bond. Specific examples include, though non-limiting, phenyl, tolyl, naphthenyl and biphenyl.

In the unsaturated substrates described herein, the term "heteroaryl" includes aromatic hydrocarbons which contain at least one heteroatom. Similar to the aryl groups, heteroaryls may have one or more aromatic rings which may be fused or connected by a connecting group or a bond.

In the unsaturated substrates described herein, the term "inert functional group" includes hydrocarbon substituents, which contain at least one heteroatom. Specific examples of these inert groups include, though not limited to, —OR$_5$ or —NR$_6$R$_7$ where R$_5$, R$_6$, R$_7$ are alkyl (C1-18, primary, secondary and tertiary alkyl), cycloalkyl (C3-C8), aryl/heteroaryl, substituted aryl/heteroaryl. Amide and ester functionality, in some cases, are tolerated by the catalysts under mild reaction conditions. High temperature and pressure conditions may result in hydrogenation of C=O bonds. In addition, substrates with ether and thioether functionalities can undergo C—O and C—S bond cleavage at elevated temperature conditions.

In the unsaturated substrates described herein, the term "heteroatom" is a Group 15 and 16 element, preferably N and O. Unsaturated substrates with halogen functionalities (F, Cl, Br and I) are not tolerated.

Reaction Substrates

As a person skilled in the art would appreciate, the class of organic compounds that can be hydrogenated or hydrosilylated is very broad. The substituents present on the substrates can be aliphatic, aromatic, unsaturated, can contain heteroatoms, can be cyclic or linear, can possess other functional groups, and/or can contain a combination of these features.

The present disclosure describes the reduction of organic substrates with at least one carbon-carbon triple bond. The types of substrates undergoing catalytic reduction are represented by the following general formula:

$$R_4 \equiv\!\!\equiv\!\!\equiv R_5$$

where:

R$^4$, R$^5$ can be the same group or different groups;

R$^4$, R$^5$ can be hydrogen, alkyl (C1-18, primary, secondary and tertiary alkyl), cycloalkyl (C3-C8), aryl/heteroaryl, substituted aryl/heteroaryl or an inert functional group containing at least one heteroatom; and wherein R$^4$, R$^5$ may also be linked by aliphatic groups to give cyclic systems;

R$^4$, R$^5$ cannot be halogens or halide-functionalized alkyl, aryl/heteroaryl.

The present disclosure describes the reduction of organic substrates with at least one carbon-carbon double bond. The types of substrates undergoing catalytic reduction are represented by the following general formula:

$$R_6\!\!-\!\!\!\underset{R_7}{\overset{H}{C}}\!\!=\!\!C\!\!-\!\!R_8$$

where:

R$^6$, R$^7$, R$^8$ can be the same group or different groups;

R$^6$, R$^7$, R$^8$ can be hydrogen, alkyl (C1-18, primary, secondary and tertiary alkyl), cycloalkyl (C3-C8), aryl/heteroaryl, substituted aryl/heteroaryl or an inert functional group containing at least one heteroatom; and wherein R$^4$, R$^5$ cannot be halogens or halide-functionalized alkyl, aryl/heteroaryl;

The substituents may also be linked to give cyclic systems, both aliphatic and aromatic [(e.g., R10/R11 or R11/R12=—(CH$_2$)$_n$—, where n=3-10].

Alkenes, in some cases, may undergo catalytic isomerization prior to or instead of hydrogenation under the reaction conditions described above.

The present disclosure describes the reduction of organic substrates with at least one carbon-oxygen double bond. The types of substrates undergoing catalytic reduction are represented by the following general formula:

$$R_9\!\!-\!\!\underset{}{\overset{O}{C}}\!\!-\!\!R_{10}$$

R$^9$, R$^{10}$ can be the same group or different groups;

R$^9$, R$^{10}$ can be hydrogen, alkyl (C1-18, primary, secondary and tertiary alkyl), cycloalkyl (C3-C8), alkenyl chain or a cycloaklyl group with unsaturated bonds, aryl/heteroaryl, substituted aryl/heteroaryl or an inert functional group optionally containing at least one heteroatom; and wherein R$^9$, R$^{10}$ may also be linked to give cyclic systems, both aliphatic and aromatic [(e.g., R1/R2=—(CH$_2$)$_n$—, where n=3-10]; and R$^4$, R$^5$ cannot be halogens or halide-functionalized alkyl, aryl/heteroaryl;

the term "heteroatom" are Group 15 and 16 elements, preferably N, S and O.

The invention is further described in the following specific examples presented for illustrative purposes only.

EXAMPLES

Example 1

Synthesis of [NiNP$^t$Bu$_3$]$_4$

A nickel phosphoranimide catalyst having the formula shown below is synthesized as an example:

$$\begin{array}{c}(^tBu)_3P\!\!=\!\!N\!\!-\!\!Ni\!\!-\!\!N\!\!=\!\!P(^tBu)_3\\ |\qquad\qquad |\\ Ni\qquad\qquad Ni\\ |\qquad\qquad |\\ (^tBu)_3P\!\!=\!\!N\!\!-\!\!Ni\!\!-\!\!N\!\!=\!\!P(^tBu)_3\end{array}$$

To prepare this catalyst (also referred to as the "Ni(I) catalyst"), NiBr$_2$(dme) (1.62 mmol) and LiNP$^t$Bu$_3$ (0.81 mmol) were separately suspended in 5 mL portions of THF in 15 mL screw-capped vials. Both suspensions were cooled to −35° C. in a drybox freezer for an hour. The LiNP$^t$Bu$_3$ suspension was added dropwise into the metal halide suspension with occasional stirring over a four-hour period with the temperature maintained at −35° C. After the addition of the ligand, the reaction mixture was left in the freezer overnight. The solvent was removed in vacuo and the residue was washed with 4 mL portions of hexane thrice. The residue was dissolved in 7 mL THF, charged with 7.5 g of 1% Na/Hg and stirred overnight. The solvent was evaporated and the product was extracted with pentane and filtered through a plug of Celite. The solvent was removed and a concentrated THF solution of the product was prepared for recrystallization. The dark green, pentane soluble solid crystallizes as prisms from a concentrated THF solution (80% yield). Elemental composition (calculated): C, 52.41%; H, 9.90%; N, 5.09%. Elemental composition (found): C, 52.38%; H, 9.89%; N, 4.96%.

Example 2

Synthesis of [NiNPCy$_3$]$_4$

NiBr$_2$(dme) (1.62 mmol) and LiNPCy$_3$ (0.81 mmol) were separately suspended in 5 mL portions of THF in 15 mL screw-capped vials. Both suspensions were cooled to −35° C. in a drybox freezer for an hour. The LiNP$^t$Bu$_3$ suspension was added dropwise into the metal halide suspension with occasional stirring over a four-hour period with the temperature maintained at −35° C. After the addition of the ligand, the reaction mixture was left in the freezer overnight. The solvent was removed in vacuo and the residue was washed with 4 mL portions of hexane thrice. The residue was dissolved in 7 mL THF, charged with 7.5 g of 1% Na/Hg and stirred overnight. The solvent was evaporated and the product was extracted with pentane and filtered through a plug of Celite. The solvent was removed and a concentrated THF solution of the product was prepared for recrystallization. The dark green, pentane soluble solid crystallizes out as prisms from a concentrated THF solution at −35° C. (65% yield).

Example 3

Synthesis of [CoNP$^t$Bu$_3$]$_4$

A cobalt phosphoranimide catalyst (also referred to herein as the "Co(I) catalyst") having the formula shown below is synthesized as an example:

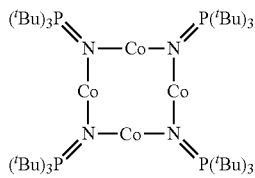

To prepare this catalyst, 1.62 mmol of CoCl$_2$ (1.62 mmol) and LiNP$^t$Bu$_3$ (0.81 mmol) were separately suspended in 5 mL portions of THF in 15 mL screw-capped vials. Both suspensions were cooled to −35° C. in a drybox freezer for an hour. The LiNP$^t$Bu$_3$ suspension was added dropwise into the metal halide suspension with occasional stirring over a four-hour period with the temperature maintained at −35° C. After the addition of the ligand, the reaction mixture was left in the freezer overnight. The solvent was removed in vacuo and the residue was washed with 4 mL portions of hexane thrice. The residue was dissolved in 7 mL THF, charged with 7.5 g of 1% Na/Hg and stirred overnight. The solvent was evaporated and the product was extracted with pentane and filtered through a plug of Celite. The solvent was removed and a concentrated THF solution of the product was prepared for recrystallization. The dark green, pentane soluble solid crystallizes out as prisms from a concentrated THF solution at −35° C. (80% yield). Elemental composition (calculated): C, 52.41%; H, 9.90%; N, 5.09%. Elemental composition (found): C, 52.38%; H, 9.89%; N, 4.96%.

Example 4

Synthesis of [FeNP$^t$Bu$_3$]$_4$

An iron phosphoranimide catalyst having the formula [Fe(NP$^t$Bu$_3$)]$_n$ was synthesized.

FeBr$_2$(dme) (1.62 mmol) and LiNP$^t$Bu$_3$ (0.81 mmol) were separately suspended in 5 mL portions of THF in 15 mL screw-capped vials. Both suspensions were cooled to −35° C. in a drybox freezer for an hour. The LiNP$^t$Bu$_3$ suspension was added dropwise into the metal halide suspension with occasional stirring over a four-hour period with the temperature maintained at −35° C. After the addition of the ligand, the reaction mixture was left in the freezer overnight. The solvent was removed in vacuo and the residue was washed with 4 mL portions of hexane thrice. The residue was dissolved in 7 mL THF, charged with 7.5 g of 1% Na/Hg and stirred overnight. The solvent was evaporated and the product was extracted with pentane and filtered through a plug of Celite. The dark brown, pentane soluble product was obtained in 45% yield.

Example 5

[CoNP$^t$Bu$_3$]$_4$-Catalyzed Hydrogenation of Allylbenzene

A 250 mL Teflon-sealing glass reactor equipped with a Teflon-covered magnetic stir bar was charged with 10 mg (0.009 mmol) of [NiNP$^t$Bu$_3$]$_4$, 150 mg (1.27 mmol) allylbenzene and 3 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rotations per minute (rpm) for 5 hours at room temperature. Excess hydrogen gas was then vented out and the reaction mixture was filtered through a plug of Florisil. The THF-fraction was subjected to GC-MS analysis. Quantitative conversion to n-propylbenzene is observed.

Example 6

[NiNP$^t$Bu$_3$]$_4$-Catalyzed Hydrogenation of Allylbenzene

A 250 mL Teflon-sealing glass reactor equipped with a Teflon-covered magnetic stirring bar was charged with 10 mg (0.009 mmol) of [NiNP$^t$Bu$_3$]$_4$, 150 mg (1.27 mmol) allylbenzene and 3 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 5 hours at room temperature. Excess hydrogen gas was then vented out and the reaction mixture was then filtered through a plug of Florisil. The THF-fraction was subjected to GC-MS analysis. Quantitative conversion to n-propylbenzene is observed.

Example 7

[NiNP$^t$Bu$_3$]$_4$-Catalyzed Hydrogenation of Trans-Stilbene

A 250 mL Teflon-sealing glass reactor equipped with a Teflon-covered magnetic stirring bar was charged with 10 mg (0.009 mmol) of [NiNP$^t$Bu$_3$]$_4$, 200 mg (1.11 mmol) trans-stilbene and 3 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 5 hours at room temperature. Excess hydrogen gas was then vented out and 3 mL of water was added. The organic product was extracted with 2 mL portions of diethyl ether thrice and the organic fractions were pooled and dried over anhydrous $Na_2SO_4$. The solvent was removed in vacuo and the solid residue was dissolved in $CDCl_3$ for $^1$H-NMR and GC-MS analysis. A $^1$H-NMR chemical shift at 3.0 ppm in $CDCl_3$ corresponds to 1,2-diphenylethane, the hydrogenation product. Quantitative conversion to 1,2-diphenylethane is observed.

Example 8

[CoNP$^r$Bu$_3$]$_4$-Catalyzed Hydrogenation of Trans-Stilbene

A 250 mL Teflon-sealing glass reactor equipped with a Teflon-covered magnetic stirring bar was charged with 10 mg (0.009 mmol) of [CoNP$^r$Bu$_3$]$_4$, 200 mg (1.11 mmol) trans-stilbene and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 5 hours at room temperature. Excess hydrogen gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1$H-NMR and GC-MS analysis. A $^1$H-NMR chemical shift at 3.0 ppm in $CDCl_3$ corresponds to 1,2-diphenylethane, the hydrogenation product. Quantitative conversion to 1,2-diphenylethane is observed.

Example 9

[NiNP$^r$Bu$_3$]$_4$-Catalyzed Hydrogenation of Cis-Stilbene

A 250 mL Teflon-sealing glass reactor equipped with a Teflon-covered magnetic stirring bar was charged with 10 mg (0.009 mmol) of [NiNP$^r$Bu$_3$]$_4$, 200 mg (1.11 mmol) cis-stilbene and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 5 hours at room temperature. Excess gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1$H-NMR and GC-MS analysis. A $^1$H-NMR chemical shift at 3.0 ppm in $CDCl_3$ corresponds to 1,2-diphenylethane, the hydrogenation product. Quantitative conversion to 1,2-diphenylethane is observed.

Example 10

[CoNP$^r$Bu$_3$]$_4$-Catalyzed Hydrogenation of Cis-Stilbene

A 250 mL Teflon-sealing glass reactor equipped with a Teflon-covered magnetic stirring bar was charged with 10 mg (0.009 mmol) of [CoNP$^r$Bu$_3$]$_4$, 200 mg (1.11 mmol) cis-stilbene and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 5 hours at room temperature. Excess gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1$H-NMR and GC-MS analysis. A $^1$H-NMR chemical shift at 3.0 ppm in $CDCl_3$ corresponds to 1,2-diphenylethane, the hydrogenation product. Quantitative conversion to 1,2-diphenylethane is observed.

Example 11

[NiNP$^r$Bu$_3$]$_4$-Catalyzed Hydrogenation of Diphenylacetylene

A 250 mL Teflon-sealing glass reactor equipped with a Teflon-covered magnetic stirring bar was charged with 10 mg (0.009 mmol) of [NiNP$^r$Bu$_3$]$_4$, 200 mg (1.12 mmol) trans-stilbene and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 8 hours at room temperature. Excess gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1$H-NMR and GC-MS analysis. Quantitative conversion to 1,2-diphenylethane is observed.

Shorter reaction times result in a mixtures containing stilbenes and 1,2-diphenylethane. $^1$H-NMR chemical shifts at 7.2 (singlet), 6.6 (singlet) and 3.0 (singlet) ppm in $CDCl_3$ correspond to hydrogenation products trans-stilbene, cis-stilbene and 1,2-diphenylethane, respectively.

Example 12

[CoNP$^r$Bu$_3$]$_4$-Catalyzed Hydrogenation of Diphenylacetylene

A 250 mL Teflon-sealing glass reactor equipped with a Teflon-covered magnetic stirring bar was charged with 10 mg (0.009 mmol) of [CoNP$^r$Bu$_3$]$_4$, 200 mg (1.12 mmol) trans-stilbene and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 8 hours at room temperature. Excess gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1$H-NMR and GC-MS analysis. Quantitative conversion to 1,2-diphenylethane is observed.

Shorter reaction times result in mixtures of stilbenes and 1,2-diphenylethane. $^1$H-NMR chemical shifts at 7.2 (singlet), 6.6 (singlet) and 3.0 (singlet) ppm in $CDCl_3$ correspond to hydrogenation products trans-stilbene, cis-stilbene and 1,2-diphenylethane, respectively.

Example 13

[NiNP$^r$Bu$_3$]$_4$-Catalyzed Hydrogenation of [(Z)-hex-3-enyl]benzoate

A 250 mL Teflon-sealing glass reactor equipped with a Teflon-covered magnetic stirring bar was charged with 10 mg (0.009 mmol) of [NiNP$^t$Bu$_3$]$_4$, 200 mg (0.98 mmol) [(Z)-hex-3-enyl]benzoate and 4 mL tetrahydrofuran (THF). The reactor was sealed and taken out of the dry box. The reactor was hooked up to a hydrogen manifold and the reactor was charged with a stream of hydrogen (1 atm). The reaction mixture was allowed to stir at a speed of 1200 rpm for 5 hours at 60° C. The reaction mixture was cooled to room temperature and excess gas was then vented. The reaction mixture was then filtered through a plug of Florisil and the THF-fraction was subjected to GC-MS analysis.

Results of the GC-MS analysis show one organic product with retention time and M$^+$ value corresponding to the hydrogenation product n-hexylbenzoate.

Example 14

[NiNP$^t$Bu$_3$]$_4$-Catalyzed Hydrogenation/Hydrosilylation of Diphenylacetylene A 250 mL Teflon-sealing glass reactor equipped with a Teflon-covered magnetic stirring bar was charged with 10 mg (0.009 mmol) of [NiNP$^t$Bu$_3$]$_4$, 200 mg (1.11 mmol) trans-stilbene, 200 mg (1.85 mmol) PhSiH$_3$ and 4 mL tetrahydrofuran (THF). The reaction mixture was allowed to stir at a speed of 1200 rpm for 5 hours at 60° C. temperature. The reaction mixture was then filtered through a plug of Florisil and the THF-fraction was subjected to GC-MS analysis.

The products under this set of reaction conditions are: cis-stilbene (4%), trans-stilbene (6.2%) and a hydrosilylation product (15%) of the formula shown below:

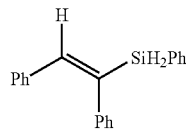

Example 15

[CoNP$^t$Bu$_3$]$_4$-Catalyzed Hydrogenation/Hydrosilylation of Allylbenzene

A 250 mL Teflon-sealing glass reactor equipped with a Teflon-covered magnetic stirring bar was charged with 10 mg (0.009 mmol) of [CoNP$^t$Bu$_3$]$_4$, 150 mg (1.27 mmol) allylbenzene, 200 mg (1.85 mmol) PhSiH$_3$ and 4 mL tetrahydrofuran (THF). The reaction mixture stirred in an oil bath at 60° C. was allowed to stir at a speed of 1200 rpm for 5 hours. The reactor was allowed to cool to room temperature. The reaction mixture was then filtered through a plug of Florisil and the THF-fraction was subjected to GC-MS analysis. Complete conversion was obtained.

The products of this reaction are: n-propylbenzene (74%), trans-1-phenylpropene (24%) and a hydrosilylation product (2%) of the formula shown below:

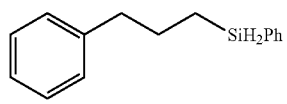

Example 16

[NiNP$^t$Bu$_3$]$_4$-Catalyzed Hydrogenation/Hydrosilylation of Allylbenzene

A 250 mL Teflon-sealing glass reactor equipped with a Teflon-covered magnetic stirring bar was charged with 10 mg (0.009 mmol) of [NiNP$^t$Bu$_3$]$_4$, 150 mg (1.27 mmol) allylbenzene, 200 mg (1.85 mmol) PhSiH$_3$ and 4 mL tetrahydrofuran (THF). The reaction mixture stirred in an oil bath at 60° C. was allowed to stir at a speed of 1200 rpm for 5 hours. The reactor was allowed to cool to room temperature. The reaction mixture was then filtered through a plug of Florisil and the THF-fraction was subjected to GC-MS analysis. Complete conversion was obtained.

The products of this reaction are: n-propylbenzene (28%), trans-1-phenylpropene (70%) and a hydrosilylation product (2%) of the formula shown below:

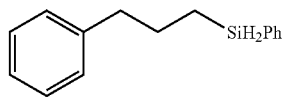

Example 17

[NiNPCy$_3$]$_4$-Catalyzed Hydrogenation of Diphenylacetylene

Synthesis of [Ni(NP$^t$Cy$_3$)]$_n$ from [Br$_2$Ni$_2$(μ-NPCy$_3$)$_2$]: 0.05 mmol of [Br$_2$Ni$_2$(μ-NPCy$_3$)$_2$] is dissolved in 5 mL THF, stirred, and then treated with 0.06 mmol of Na using a 1% a(Hg) reagent at −35° C. to room temperature 2 hours. The THF fraction of the mixture is separated from any remaining solid components.

The THF fraction is used directly as dissolved catalyst and solvent for the hydrogenation of 1,2-diphenylacetylene. A 250 mL Teflon-sealing glass reactor equipped with a Teflon-covered magnetic stirring bar was charged with 4 mL of the THF solution from the previous step and 200 mg (1.11 mmol) trans-stilbene. The reactor was sealed and taken out of the dry box. The reactor was hooked up to a hydrogen manifold and the reactor was charged with a stream of hydrogen (1 atm). The reaction mixture was allowed to stir for 10 hours at room temperature. Excess gas was then vented out and 3 mL of water was added. The organic product was extracted with 2 mL portions of diethyl ether thrice and the organic fractions were pooled and dried with anhydrous Na$_2$SO$_4$. The solvent was removed in vacuo and the solid residue was dissolved in CDCl$_3$ for $^1$H-NMR and GC-MS analysis. Quantitative conversion to 1,2-diphenylethane is observed.

Shorter reaction times result in a mixture of stilbenes and 1,2-diphenylethane. $^1$H-NMR chemical shifts at 7.2 (singlet), 6.6 (singlet) and 3.0 (singlet) ppm in CDCl$_3$ correspond to hydrogenation products trans-stilbene, cis-stilbene and 1,2-diphenylethane, respectively.

Example 18

[FeNP$^t$Bu$_3$]$_4$-Catalyzed Hydrogenation of Diphenylacetylene

Synthesis of [Fe(NP$^t$Bu$_3$)]$_4$ from [Br$_2$Fe$_2$(μ-NP$^t$Bu$_3$)$_2$]: 0.05 mmol of [Br$_2$Fe$_2$(μ-NPt-Bu$_3$)$_2$] is dissolved in 5 mL THF, stirred, and then treated with 0.05 mmol of Na using a 1% Na(Hg) reagent at −35° C. to room temperature 2 hours. The THF fraction of the mixture is separated from any remaining solid components.

The THF fraction is used directly as dissolved catalyst and solvent for the hydrogenation of 1,2-diphenylacetylene. A 250 mL Teflon-sealing glass reactor equipped with a Teflon-covered magnetic stirring bar was charged with 4 mL of the THF solution from the previous step and 200 mg (1.11 mmol) trans-stilbene. The reactor was sealed and taken out of the dry box. The reactor was hooked up to a hydrogen manifold and the reactor was charged with a stream of hydrogen (1 atm). The reaction mixture was allowed to stir for 30 minutes at room temperature. Excess gas was then vented out and 3 mL of water was added. The organic product was extracted with 2 mL portions of diethyl ether thrice and the organic fractions were pooled and dried with anhydrous $Na_2SO_4$. The solvent was removed in vacuo and the solid residue was dissolved in $CDCl_3$ for $^1H$-NMR and GC-MS analysis. A conversion of 11% was obtained. The products of this reaction are: trans-stilbene (4%) and cis-stilbene (7%).

Example 19

[FeNP$^t$Bu$_3$]$_4$-Catalyzed Hydrogenation/Hydrosilylation of Diphenylacetylene The method of synthesis of [BrFe(NP$^t$Bu$_3$)]$_2$ is described in a co-pending application.

Synthesis of [Fe(NP$^t$Bu$_3$)]$_4$ from [Br$_2$Fe$_2$(μ-NP$^t$Bu$_3$)$_2$]: 0.08 mmol of [Br$_2$Fe$_2$(μ-NP$^t$Bu$_3$)$_2$] is dissolved in 5 mL THF, stirred, and then treated with 0.08 mmol of Na using a 1% Na(Hg) reagent at −35° C. to room temperature 2 hours. The THF fraction of the mixture is separated from any remaining solid components.

A 250 mL Teflon-sealing glass reactor equipped with a Teflon-covered magnetic stirr bar was charged with 4 mL of the THF solution from the previous step, 200 mg (1.11 mmol) trans-stilbene, 200 mg (1.85 mmol) PhSiH$_3$ and an addition 2 mL THF. The reaction mixture was allowed to stir for 5 hours at room temperature. The reaction mixture was then filtered through a plug of Florisil and the THF-fraction was subjected to GC-MS analysis. A 14% substrate conversion was obtained.

The products of this reaction are: cis-stilbene (7%), trans-stilbene (4%) and the hydrosilylation product (3%) of the formula shown below:

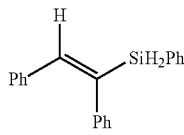

Example 20

[NiNP$^t$Bu$_3$]$_4$-Catalyzed Hydrogenation/Hydrosilylation of Cycloheptanone

A 250 mL Teflon-sealing glass reactor equipped with a Teflon-covered magnetic stirr bar was charged with 10 mg (0.009 mmol) of [NiNP$^t$Bu$_3$]$_4$, 200 mg (1.78 mmol) cycloheptanone, 200 mg (1.85 mmol) PhSiH$_3$ and 4 mL tetrahydrofuran (THF). The reaction mixture was allowed to stir at a speed of 1200 rpm for 16 hours at 60° C. temperature. The reaction mixture was then filtered through a plug of Florisil and the THF-fraction was subjected to GC-MS analysis. A conversion of 96% was obtained.

The products of this reaction under these conditions:

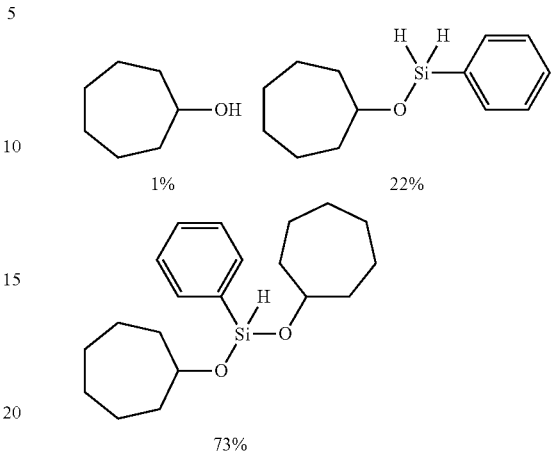

Example 21

[NiNP$^t$Bu$_3$]$_4$-Catalyzed Hydrogenation/Hydrosilylation of 4-ethylacetophenone A 250 mL Teflon-sealing glass reactor equipped with a Teflon-covered magnetic stirr bar was charged with 10 mg (0.009 mmol) of [NiNP$^t$Bu$_3$]$_4$, 200 mg (1.35 mmol) 4-ethylacetophenone, 200 mg (1.85 mmol) PhSiH$_3$ and 4 mL tetrahydrofuran (THF). The reaction mixture was allowed to stir at a speed of 1200 rpm for 16 hours at 60° C. temperature. The reaction mixture was then filtered through a plug of Florisil and the THF-fraction was subjected to GC-MS analysis.

The major products of this reaction are the following alkoxysilanes:

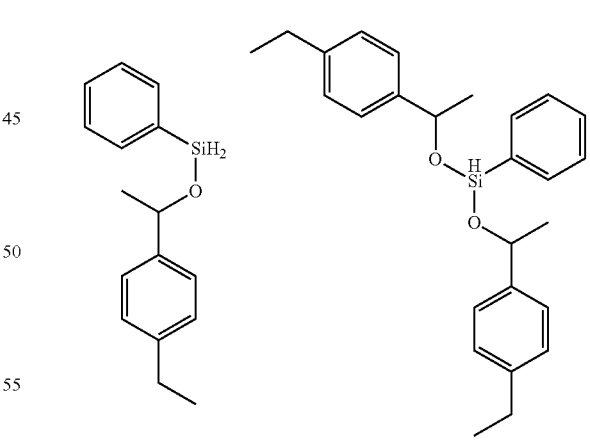

Example 22

[NiNP$^t$Bu$_3$]$^4$-Catalyzed Hydrogenation of 4-ethylacetophenone

A 250 mL Teflon-sealing glass reactor equipped with a Teflon-covered magnetic stir bar was charged with 10 mg (0.009 mmol) of [NiNP$^t$Bu$_3$]$_4$, 200 mg (1.35 mmol) 4-ethylacetophenone, 145 mg (1.35 mmol) PhSiH$_3$ and 4 mL tetrahydrofuran (THF). The reactor was sealed and taken out of the dry box. The reactor was attached to a hydrogen manifold and the reactor was charged with a stream of hydrogen (1 atm). The reaction mixture was allowed to stir at a speed of 1200 rpm for 16 hours at 60° C. temperature. The reaction mixture was cooled to room temperature and excess gas was vented off. The reaction mixture was then filtered through a plug of Florisil and the THF-fraction was subjected to GC-MS analysis. A 86% conversion to the following alcohol was observed:

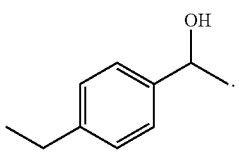

The invention claimed is:

1. A method of catalyzing a hydrogenation or hydrosilyation reaction comprising: reacting a organic substrate having at least one unsaturated group in the presence of a reducing agent with a catalyst of general formula:

[M(NPR$_3$)]$_n$ where:
M is a first row transition metal having a +1 oxidation state;
n is a whole number of 2 or greater;
R$_3$PN$^-$ is a monoanioinic phosphoranimide ligand of structure:

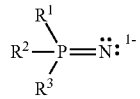

where:
R$^1$, R$^2$, R$^3$ are the same group or different groups;
R$^1$, R$^2$, R$^3$=alkyl (C1-18, primary, secondary and tertiary alkyl), cycloalkyl (C3-C8), aryl/heteroaryl, substituted aryl/heteroaryl or an inert functional group containing at least one heteroatom; or
R$^1$, R$^2$, R$^3$ are linked to give cyclic systems; and
wherein the M to R$_3$PN$^-$ ratio is 1:1.

2. The method of claim 1, wherein M is selected from the group consisting of Fe, Co and Ni.

3. The method of claim 1, wherein R$^1$, R$^2$, R$^3$ are alkyl groups selected from the group consisting of methyl, ethyl, n-propyl, isopropyl, sec-butyl and t-butyl.

4. The method of claim 1, wherein R$^1$, R$^2$, R$^3$ are t-butyl.

5. The method of claim 1, wherein R$^1$, R$^2$, R$^3$ are cycloalkyl groups selected from the group consisting of cyclopentyl, cyclohexyl, alkyl-substituted cyclopentyl and alkyl-substituted cyclohexyl.

6. The method of claim 5 wherein R$^1$, R$^2$, R$^3$ are selected from the group consisting of cyclohexyl and cyclopentyl.

7. The method of claim 1 wherein R$^1$, R$^2$, R$^3$ are aryl groups selected from the group consisting of phenyl, tolyl, xylyl, naphthanyl and biphenyl.

8. The method of claim 1, wherein the substrate is an internal alkyne, or a derivative thereof, having the general formula:

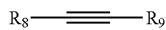

where:
R$^8$, R$^9$ are the same group or different groups;
R$^8$, R$^9$ are hydrogen, alkyl (C1-18, primary, secondary and tertiary alkyl), cycloalkyl (C3-C8), aryl/heteroaryl, substituted aryl/heteroaryl or an inert functional group containing at least one heteroatom; or
R$^8$, R$^9$ are linked to give cyclic systems, both aliphatic and aromatic.

9. The method of claim 1, wherein the substrate is an alkene, or a derivative thereof, having the general formula:

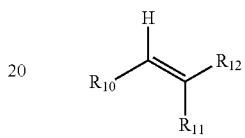

where:
R$^{10}$, R$^{11}$, R$^{12}$ are the same group or different groups;
R$^{10}$, R$^{11}$, R$^{12}$ are H, alkyl (C1-18, primary, secondary and tertiary alkyl), cycloalkyl (C3-C8), aryl/heteroaryl, substituted aryl/heteroaryl or an inert functional group containing at least one heteroatom; or
wherein the substituents are linked to give cyclic systems, both aliphatic and aromatic and
wherein R10/R11 or R11/R12=—(CH$_2$)$_n$—, where n=3-1.

10. The method of claim 1, wherein the substrate is a ketone, or a derivative thereof, having the general formula:

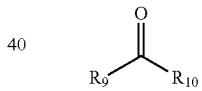

R$^9$, R$^{10}$ are the same group or different groups;
R$^9$, R$^{10}$ are hydrogen, alkyl (C1-18, primary, secondary and tertiary alkyl), cycloalkyl (C3-C8), alkenyl chain or a cycloalkyl group with unsaturated bonds, aryl/heteroaryl, substituted aryl/heteroaryl or an inert functional group optionally containing at least one heteroatom; or
R$^9$, R$^{10}$ are linked to give cyclic systems, both aliphatic and aromatic.

11. The method of claim 1, wherein the ratio of substrate to catalyst ranges from 1000:1 to less than 1:1.

12. The method of claim 1, wherein the reducing agent is selected from the group consisting of H$_2$ and an organic silyl hydride.

13. The method of claim 1, further comprising carrying out the reaction under H$_2$ pressures of ≤1 atm to 100 atm.

14. The method of claim 1, further comprising carrying out the reaction in the presence of an inert solvent selected from the group consisting of an alkyl solvent, an aromatic hydrocarbon solvent and an alkyl ether solvent.

15. The method of claim 1, wherein the catalyst is selected from the group consisting of [Ni(NP$^t$Bu$_3$)]$_4$, [Co(NP$^t$Bu$_3$)]$_4$ and [Fe (NP$^t$Bu$_3$)]$_4$.

16. A method of catalyzing the hydrogenation or hydrosilylation of an organic compound having at least one unsaturated group comprising:
reacting the organic substrate with a compound selected from the group consisting of [Fe(NP$^t$Bu$_3$)]$_4$, [Co(NP$^t$Bu$_3$)]$_4$ and [Ni(NP$^t$Bu$_3$)]$_4$.

17. A process for hydrogenation of an organic substrate having at least one unsaturated group:
(i) combining the organic substrate with a transition metal catalyst and a reductant to obtain a reaction medium;
(ii) allowing the catalyst to catalyze the hydrogenation of the substrate;
(iii) obtaining the reduced products from the organic substrate;
wherein the organic substrate is a compound containing at least one unsaturated group;
wherein the ratio of catalyst to substrate is less than 1:1; and
wherein the catalyst has the formula:

[M(NPR$_3$)]$_n$ where
n is a whole number of 2 or greater;
the ratio of M to NPR$_3$ is 1:1;
M is a first row transition metal selected from the group consisting of Fe, Co and Ni;
NPR$_3$ is:

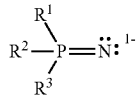

where:
R$^1$, R$^2$, R$^3$ are independently alkyl (C1-18, primary, secondary or tertiary alkyl), cycloalkyl (C3-C8), aryl/heteroaryl, substituted aryl/heteroaryl or an inert functional group containing at least one heteroatom selected from the group consisting of a Group 14, Group 15 and Group 16 element; and wherein R$^1$, R$^2$, R$^3$ may also be linked by aliphatic groups to give cyclic systems.

18. The process of claim 17, wherein the substrate contains at least one double bond.

19. The process of claim 17, wherein the substrate contains at least one triple bond.

* * * * *